US007390301B2

(12) United States Patent
Skrabal et al.

(10) Patent No.: US 7,390,301 B2
(45) Date of Patent: Jun. 24, 2008

(54) DEVICE AND METHOD FOR THE CONTINUOUS NON-INVASIVE MEASUREMENT OF BLOOD PRESSURE

(75) Inventors: Falko Skrabal, Graz (AT); Jürgen Fortin, Graz (AT)

(73) Assignee: Cnsystems Medizintechnik GmbH, Graz (AT)

( * ) Notice: Subject to any disclaimer, the term of this patent is extended or adjusted under 35 U.S.C. 154(b) by 93 days.

(21) Appl. No.: 10/551,189

(22) PCT Filed: Apr. 1, 2004

(86) PCT No.: PCT/AT2004/000117

§ 371 (c)(1),
(2), (4) Date: Sep. 29, 2005

(87) PCT Pub. No.: WO2004/086963

PCT Pub. Date: Oct. 14, 2004

(65) Prior Publication Data

US 2006/0195034 A1 Aug. 31, 2006

(30) Foreign Application Priority Data

Apr. 1, 2003 (AT) ............................... A 509/2003

(51) Int. Cl.
*A61B 5/02* (2006.01)
(52) U.S. Cl. ..................... 600/490; 600/500; 600/493; 600/494
(58) Field of Classification Search ................. 600/481, 600/483–486, 490–507, 488
See application file for complete search history.

(56) References Cited

U.S. PATENT DOCUMENTS 5,025,792 A 6/1991 Hon et al.

(Continued)

FOREIGN PATENT DOCUMENTS

EP 1 125 546 9/1999

(Continued)

OTHER PUBLICATIONS

J. Penaz et al., "Vibration Plethysmography: A Method for Studying the Visco-Elastic Properties of Finger Arteries" in Medical & Biological Eng. & Computing, vol. 35, No. 6, Nov. 1997, pp. 633-637.

(Continued)

*Primary Examiner*—Charles A. Marmor, II
*Assistant Examiner*—Navin Natnithithadha
(74) *Attorney, Agent, or Firm*—Dykema Gossett PLLC

(57) ABSTRACT

A method for the continuous non-invasive measurement of blood pressure includes at least one first pressure cuff and one second pressure cuff of comparable or identical size, each cuff including an inflatable pressure measuring chamber applicable to a first and a second body part or region containing an artery. The first pressure cuff has a first plethysmographic sensor connected to a regulating and control device used to regulate the pressure in a first pressure measuring chamber by means of a measuring signal of the plethysmographic sensor. The first pressure measuring chamber is connected to a pressure sensor in order to obtain a pressure measuring signal. The second pressure measuring chamber is a reference pressure chamber that can be regulated at the same time as the first pressure measuring chamber, independently therefrom, and can be regulated by the regulating and control device according to a pre-determinable pressure function.

5 Claims, 5 Drawing Sheets

U.S. PATENT DOCUMENTS

| | | |
|---|---|---|
| 5,048,533 A | 9/1991 | Muz |
| 5,152,296 A * | 10/1992 | Simons .................. 600/483 |
| 6,120,459 A * | 9/2000 | Nitzan et al. ............ 600/493 |
| 6,322,515 B1 * | 11/2001 | Goor et al. .............. 600/485 |
| 6,440,079 B1 * | 8/2002 | Ogura et al. ............ 600/492 |
| 6,669,646 B1 * | 12/2003 | Narimatsu et al. ...... 600/485 |
| 6,669,648 B1 | 12/2003 | Fortin et al. |
| 6,796,946 B2 * | 9/2004 | Ogura et al. ............ 600/500 |
| 2004/0039290 A1 * | 2/2004 | Narimatsu et al. ...... 600/490 |

FOREIGN PATENT DOCUMENTS

| | | |
|---|---|---|
| WO | 00/59369 | 10/2000 |

OTHER PUBLICATIONS

English Abstract of DE 3935939.
English Abstract of EP 0377554.

* cited by examiner

DEVICE AND METHOD FOR THE CONTINUOUS NON-INVASIVE MEASUREMENT OF BLOOD PRESSURE

BACKGROUND OF THE INVENTION

FIELD OF THE INVENTION

The invention relates to a method and device for continuous, non-invasive measurement of blood pressure based on the principle of the unloaded arterial wall, where on at least one first and one second body part or body region, each containing an artery of identical or comparable size, there is positioned one first and one second pressure cuff of identical or comparable size with one first and one second inflatable pressure measuring chamber, the pressure in the first pressure measuring chamber being controlled in dependence of the measurement signal of a plethysmographic sensor device in such a way that the amplitude of the plethysmographic measurement signal is minimized, and a pressure measurement signal being obtained from the first pressure measurement chamber.

THE PRIOR ART

In medical practice it is often necessary to measure continuously the blood pressure of living beings. Non-invasive measurement avoiding the puncture of arteries is particularly advantageous in this context. One non-invasive technique which has proved to be of particular worth, is the "vascular unloading technique" (also designated as principle of the relaxed or unloaded arterial wall), in which the blood volume or blood flow in an extremity such as a finger, which varies in a pulsatil manner with heartbeat, is measured plethysmographically, e.g. by means of an optical sensor device consisting of light emitter and light detector.

In this method the pressure in the pressure chamber of an inflatable cuff, which is externally placed over an artery and which transmits its controlled pressure to the underlying artery, is varied via a feedback loop in dependence of the plethysmographic signal in such a way that the blood volume or blood flow, which formerly has pulsated, will now remain constant or the pulsating variations will at least be minimized. To this end the pressure in the cuff is increased during the systolic phase, when blood flow or volume is larger, and is decreased during the diastolic phase with its lower blood flow or volume. This will completely relieve the tension in the artery wall, and in the artery and the cuff which are now separated only by a freely floating membrane (=the unloaded artery wall), equal pressures will prevail as in communicating vessels, while the so-called transmural pressure $P_{Tm}$ is zero. The pressure $P_M$ measured in the measurement chamber is thus directly equal to the arterial blood pressure $P_{B1}$ of the pulse curve, as can be seen from the equation $$P_M = P_{B1} - P_{Tm} \text{ with } P_{Tm} = 0.$$

In the context of the "vascular unloading technique" the term closed-loop measurement is used if the cuff pressure is controlled by the plethysmographic signal (closed feedback loop), and the term open-loop measurement is used if the cuff pressure is constant or is adjusted independently of the plethysmographic signal.

Following are references for the "vascular unloading technique"; D1: J. PENAZ: Photoelectric Measurement of Blood Pressure, Volume and Flow in the Finger, Digest of the 10$^{th}$ International Conference on Medical and Biological Engineering 1973 Dresden; D2: G. P. MOLHOEK, K. H. WESSELING, J. J. M. SETTELS, E. VAN VOLLENHOVEN, H. WEEDA, B. DE WITT, A. C. ARNTZENIUS: Evaluation of the Penaz servo-plethysmo-manometer for the continuous, non-invasive measurement of finger blood pressure, Basic Res. Cardiol., 79: 598-609, 1984; D3: J. C. DORLAS, J. A. NIJBOER, W. T. BUTJIN, M. A. VAN DER HOEVEN, J. J. SETTELS, K. H. WESSELING: Effects of Peripheral Vasoconstriction on the Blood Pressure in the Finger, Measured Continuously by a New Noninvasive Method (The Finapres®), Anesthesiology 62: 342-345, 1985;

In order to find the optimum pressure of the pressure chamber prior to the actual measurement, it is known to determine a so-called "setpoint" by means of pressure changes in the shape of a pressure ramp or a pressure stairway before the feedback loop is closed. The setpoint chosen in this way will be roughly that pressure of the measuring chamber for which the amplitude of the plethysmographic signal (i.e. the signal of the light detector) is at or at least near its maximum value (see e-g. D1, D3).

From WO 00/59369 A2 and AT 408.066 B a continuous, non-invasive blood pressure measuring device has become known, which is based on the principle of the unloaded arterial wall and which comprises a double finger cuff for adjacent fingers. The pressure chambers in the two cuffs are controlled by the measuring signal of a plethysmographic sensor device, each consisting e.g. of a light emitter and light detector, with both pressure chambers connected to a common pressure control chamber. By means of a switch valve pressure may be applied alternatively either to the first or the second cuff. The common pressure control chamber is furnished with separate inlet and outlet valves, such that the pressure of the pressure control chamber may promptly follow the steering information of the plethysmographic measuring signal.

When the feedback loop is closed, the setpoint can no longer be checked properly. It is therefore necessary in the known methods to intermittently interrupt the continuous measurement for readjustment of the setpoint, or the setpoint may be lost during measurement, which may result in false indication of a drop or rise in blood pressure. Under these circumstances the user is unable to decide whether an observed change in blood pressure or blood pressure amplitude is caused by a physiological or pathological change of intra-arterial blood pressure or by a shift of the setpoint. This has made the method unsuitable for application in intensive care units or in the operating theatre where it would be most urgently needed.

From DE 38 29 456 A1 a blood pressure measuring device with two cuffs for the upper arms is known, which both work at slightly different pressures a little below diastolic blood pressure. In a variant the two cuffs may be configured as a double finger cuff. Pressure measurement is however not based on the preferred vascular unloading technique as described above.

In DE 39 35 939 A1 a non-invasive blood pressure measuring device is described, which employs an optical converter to obtain a blood pressure signal and where a conventional electronic blood pressure cuff is used for calibrating the measuring device.

From ES 0 377 554 A1 a method for measuring blood pressure is known, in which the blood pressure is measured at least at one location and at a reference location. The phase shift between the blood pressure signals obtained at the measuring location and at the reference location is used to compute the blood pressure.

It is an object of the present invention to improve the above described methods and devices for the continuous, non-invasive measurement of blood pressure using the vascular unloading technique in such a way that it can be decided reliably whether an observed change in blood pressure or blood pressure amplitude is due to a physiological or pathological change of intra-arterial blood pressure or is caused by a shift of the setpoint.

According to the invention this object is achieved by providing that the second pressure measuring chamber is used a reference pressure chamber independently of the first pressure measuring chamber, and that the pressure in the reference pressure chamber is controlled according to a pre-selectable pressure function and a reference signal is obtained simultaneously with the measured pressure signal, and that the reference signal is used in the interpreting of the measured pressure signal.

A device for implementation of the method of the invention is characterised in that the pressure measuring chamber of the second pressure cuff is configured as a reference pressure chamber which can be controlled simultaneously with and independently of the pressure measuring chamber of the first pressure cuff, and that the pressure measuring chamber of the first pressure cuff and the reference pressure chamber of the second pressure cuff each have separate inlet and outlet valves, with the pressure in the reference pressure chamber being controllable in accordance with a pre-selectable pressure function by means of a control unit. It is thus possible to obtain a measured pressure signal and a reference signal simultaneously.

The present invention thus avoids the disadvantages mentioned above by providing the possibility of simultaneously and continuously monitoring the closed-loop blood pressure measurement by means of a "watchdog" unit, i.e. the open-loop measurement in the reference chamber. To this end similarly or identically dimensioned or configured pressure chambers must be placed over arteries of similar or identical dimension. The double finger cuff described in WO 00/59369 A2 is particularly suitable for this purpose but has to be adapted for the needs of the present invention, primarily by providing the pressure measuring chamber of the first pressure cuff and the reference pressure chamber of the second pressure cuff each with separate inlet and outlet valves.

Although the pressure measuring chamber and the reference pressure chamber in principle may be placed over diverse arteries, for instance over the arteria temporalis and arteria radialis, it is of particular advantage—especially for long-time measurement—if both pressure cuffs are placed over neighbouring arteries, preferably those of two adjacent fingers of one hand. The other hand will thus be freely accessible for necessary intensive care purposes.

The reference signal in the reference pressure chamber may be measured oscillometrically or preferably plethysmographically by means of a pressure sensor located in this area, if according to two variants of the invention the second pressure cuff is provided with an oscillometric, or preferably, a second plethysmographic sensor device. If a plethysmographic sensor is not provided in the reference pressure chamber, only the amplitude of the pressure oscillations caused by the arterial pulse at diverse applied pressure values may be measured, as known from conventional oscillatory blood pressure measurement. The maximum of the oscillations corresponds to the arterial mean pressure.

The essentially identical pressure chambers and light emitting and detecting means of the plethysmographic sensor devices of the two cuffs as proposed by the invention have simultaneously complementary functions. When the plethysmographic sensor device of one pressure measuring chamber is switched to the "closed-loop" state and controls the chamber pressure such that the light signal is constant and transmural pressure $P_{Tm}$ is equal or near zero, the other pressure chamber is switched to open-loop operation ("watchdog") and vice versa.

According to the invention the pressure in the reference pressure chamber may be varied in the form of a repeating staircase or ramp function. The reference pressure chamber is intermittently subjected to pressure changes, e.g. pressure ramps or stairs, in order to continuously monitor or adjust the setpoint, respectively to discriminate between drifts of the setpoint and actual physiological or pathological drifting of the arterial blood pressure.

In a further particularly advantageous development of the invention at least two differing monitoring states are proposed: a first state in which the change of the plethysmographic reference signal caused by applying a preselectable pressure function, e.g. a pressure staircase function to the reference pressure chamber, is only observed (open-loop), and a second monitoring state in which the pressure in the reference pressure chamber is controlled by means of the preselectable pressure function and at the same time by means of the plethysmographically obtained reference signal in such a way that the amplitude of the reference signal is minimized, while a reference pressure signal is measured (semi-closed-loop). It is attempted to minimize the plethysmographic signal also during the pressure change, i.e. while the staircase function is applied. In the following the first of the two states of the reference pressure chamber is referred to as open-loop-stair, the second as semi-closed-loop-stair, while the state of the pressure measuring chamber is referred to as closed-loop. By means of this arrangement the setpoint of the closed-loop pressure measuring chamber may continuously be controlled and adjusted by the watchdog or reference pressure chamber, and actual blood pressure changes in the body may absolutely reliably be discriminated from a shift of the setpoint.

It is provided by the invention that a loss of the setpoint of the pressure signal is inferred if a change of the mean pressure and/or the amplitude of the pressure measuring signal occurs and the amplitude maximum of the reference signal or reference pressure signal is either not shifted at all, or is shifted in the opposite direction.

Due to the completely identical construction of the pressure chambers of the two pressure cuffs it is possible to operate the reference pressure chamber as pressure measuring chamber and the latter as reference pressure chamber either during predetermined periods of time or if the setpoint is lost. Thus the watchdog pressure chamber may at any time be switched to act as closed-loop pressure measuring chamber and vice versa. This arrangement also has the great advantage that the part of the body, e.g. the finger, which is used for closed-loop measurement, may repeatedly be changed either automatically or manually, without interrupting the recorded pulse curve. It is only necessary immediately before switch-over to use the last setpoint obtained in the reference pressure chamber to determine the setpoint for the closed-loop measurement and then to switch to closed-loop measurement of blood pressure on this finger, before closed-loop measurement on the other finger is ended. The other finger subsequently is used to find and monitor the setpoint.

From a change of the mean pressure and/or of the amplitude of the pressure measuring signal and a shift of the amplitude maximum of the reference signal or reference pressure signal in the same direction, a physiological or pathological change of the pressure measuring signal may be inferred according to the invention. Pertinent details are explained in the discussion of the diagrams of FIG. 3 and FIG. 4.

According to the invention the reference pressure signal measured at different preselectable pressure values of the pressure function may be analysed, and compared to given ideal pulse curves, and when a minimum deviation from a given pulse curve is found, the setpoint for the pressure measuring signal may be determined therefrom.

Before the printing of the pressure curve the control and adjusting unit, which preferably should be a microprocessor, should adjust the subsequent blood pressure curve to the preceding blood pressure curve regarding absolute height as well as amplitude. This should only be done, however, if planned, routine switching is carried out, but not if uncorrected setpoint shifts have previously occurred. This new method will significantly reduce pressure load and blood congestion in both fingers, while measurement of the pressure curve is carried out free of interruption, and genuine pressure changes in the body may for the first time be discriminated online from setpoint shifts with absolute certainty. The resulting great advantages make this non-invasive measurement of a continuous pulse curve for the first time suitable for patient monitoring in intensive care units or in the operating theatre.

The invention will now be explained in more detail with reference to the enclosed drawings.

DETAILED DESCRIPTION OF THE PREFERRED EMBODIMENTS

Figure 1:
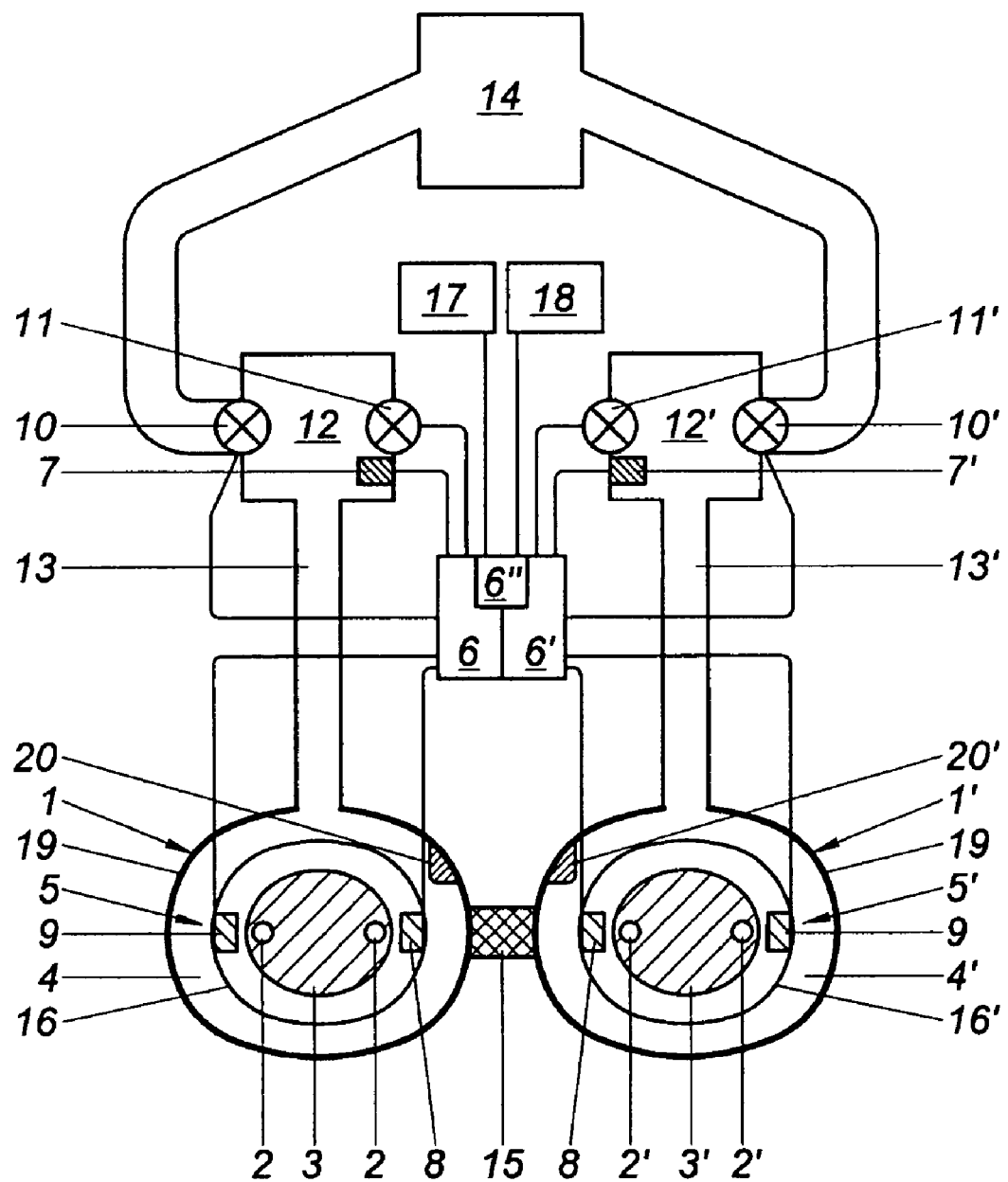
FIG. 1 is schematic view of the device of the invention for the continuous, non-invasive measurement of blood pressure based in the principle of the unloaded arterial wall.

FIG. 1 shows a device for the continuous, non-invasive measurement of blood pressure, with at least one first pressure cuff 1, which can be attached to a first body part or body region 3 containing an artery 2, and which comprises an inflatable pressure measuring chamber 4 and a first plethysmographic sensor device 5, and where a control and adjusting unit 6 is provided, which controls the pressure in the pressure measuring chamber 4 by means of the measurement signal of the plethysmographic sensor device 5, in such a way that the amplitude of the plethysmographic measurement signal is minimized. The pressure measuring chamber 4 is connected with a least one pressure sensor 7 to obtain a pressure measuring signal. The device of the invention has a second pressure cuff 1', which can be attached to a second body part or body region 3' containing an artery 2', and which comprises an inflatable reference pressure chamber 4' (watchdog pressure chamber) of the same design as the pressure measuring chamber 4, with a pressure sensor 7'. The pressure in the reference pressure chamber 4' is controlled by the control and adjusting unit 6 in accordance with a preselected pressure function. The second pressure cuff 1' comprises a second plethysmographic sensor unit 5'.

In the example shown the plethysmographic sensor devices 5, 5' are each furnished with light emitters 8 and light detectors 9 and are thus able to detect the pulsating changes of the irradiated volume. The separate inlet valves 10, 10' and outlet valves 11, 11' of the pressure measuring chamber 4 and the reference pressure chamber 4' are placed in separate pressure control chambers 12, 12', which are connected by pressure lines 13, 13' to the pressure measuring chamber 4 and the reference pressure chamber 4' and, via inlet valves 10, 10', to a common pressure source 14. It would also be possible to position the inlet valves 10, 10', outlet valves 11, 11', and the pressure sensors 7, 7' directly in the pressure measuring chamber 4 and reference pressure chamber 4', respectively, thereby eliminating the pressure control chambers 12, 12'.

The two pressure cuffs 1, 1' are preferably configured ring-shaped and are essentially rigidly connected by the connecting element 15, forming a double finger cuff. The pressure chambers 4, 4' are each provided on the inside with an easily deformable membrane 16, 16'. The rigid connection 15 has the advantage that the light emitters 3 and light detectors 9 of the plethysmographic sensor devices 5, 5', which are located between pressure chamber 4, 4' and the respective finger 3, 3', are kept in constant and optimum position regarding the respective artery 2, 2'. Prior to measurement it is only necessary to slip the two ring-shaped pressure chambers 4, 4' of the double finger cuff onto the fingers 3, 3', whereby the proper positioning of light emitters 8 and light detectors 9 is guaranteed. The separate inlet and outlet valves 10, 11 and 10', 11' of the two pressure control chambers 12, 12' are controlled by a control and adjusting unit consisting for instance of one or more microprocessors 6, 6', 6".

The control and adjusting unit simultaneously accomplishes diverse tasks. Different processors 6 or 6' may be used to simultaneously run different control tasks, or a multi-tasking or multi-threading processor 6, 6' may be used. A supervisor unit 6" coordinates the individual tasks and takes care of emergency interrupts and displays. The pressure measuring chamber 4 and the reference pressure chamber 4' may thus be pressurized differently, using the same pressure source 14. The control and adjusting unit serves a display unit 17 and an alarm unit 18. In order to reduce the compliance of the two pressure chambers 4, 4' it is of advantage if these are provided with a relatively rigid wall 19 on the outside not adjacent to the body part. Into or onto each of this compliance-reducing rigid walls at least one temperature sensor 20, 20' may also be placed.

Figure 2:
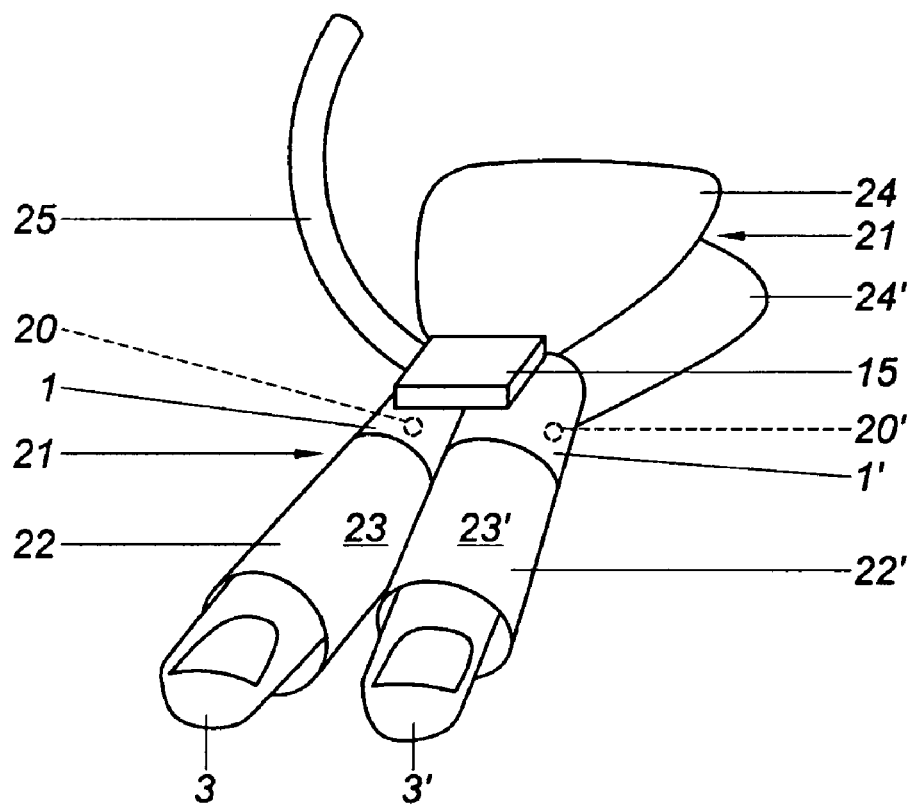
FIG. 2 shows details of a variant of the device according to FIG. 1.

As shown in the variant of FIG. 2 a heating unit 21 may also be either integrated in or attached to the two pressure cuffs 1, 1', which heating unit has at least one heating element 22, 22', preferably a heating spiral or heating foil. The heating unit 21 may also be designed to be attachable to the double finger cuff. The pressure chamber or the part of the body whose artery is to be measured, e.g. the finger 3 or 3', may thus be warmed in such a way that even centralisation of blood circulation, as for instance under shock, will not lead to a loss of the volume or flow signal of the two plethysmographic sensor devices 5, 5' in the two pressure chambers of the pressure cuffs 1, 1'. Besides furnishing physiological temperatures of roughly 37° C., the heating unit may be used to produce more intense heat if heat-induced hyperaemia is to be utilized.

The heating unit 21 may also have heatable appendages, for instance fingerstalls 23, 23', which extend distally towards the body periphery. These fingerstalls may extend as far as the finger tips or near the finger tips. The heating unit 21 may further have appendages 24, 24' extending proximally towards the body centre, which lie for instance against, the inside of the hand and against the back of the hand. The heating unit could also be shaped like a mitten enclosing more than one finger or it may be sheet-shaped and fastened around the hand by a touch-and-close fastener. When used in an intensive care unit it is of advantage if at least the finger tips are left free to permit the physician to judge blood circulation and oxygen saturation.

It is advantageous to provide a common tube 25 containing pneumatic feeds and electrical lines for both pressure cuffs 1, 1' and for the heating unit 21, since especially in the operating theatre and in intensive care units each additional line is a hindrance. The heating unit 21 may have at least one temperature sensor 20, 20' placed in one of the pressure cuffs 1, 1', whose temperature signal is used for controlling the heat output of the heating unit 21.

Figure 3:
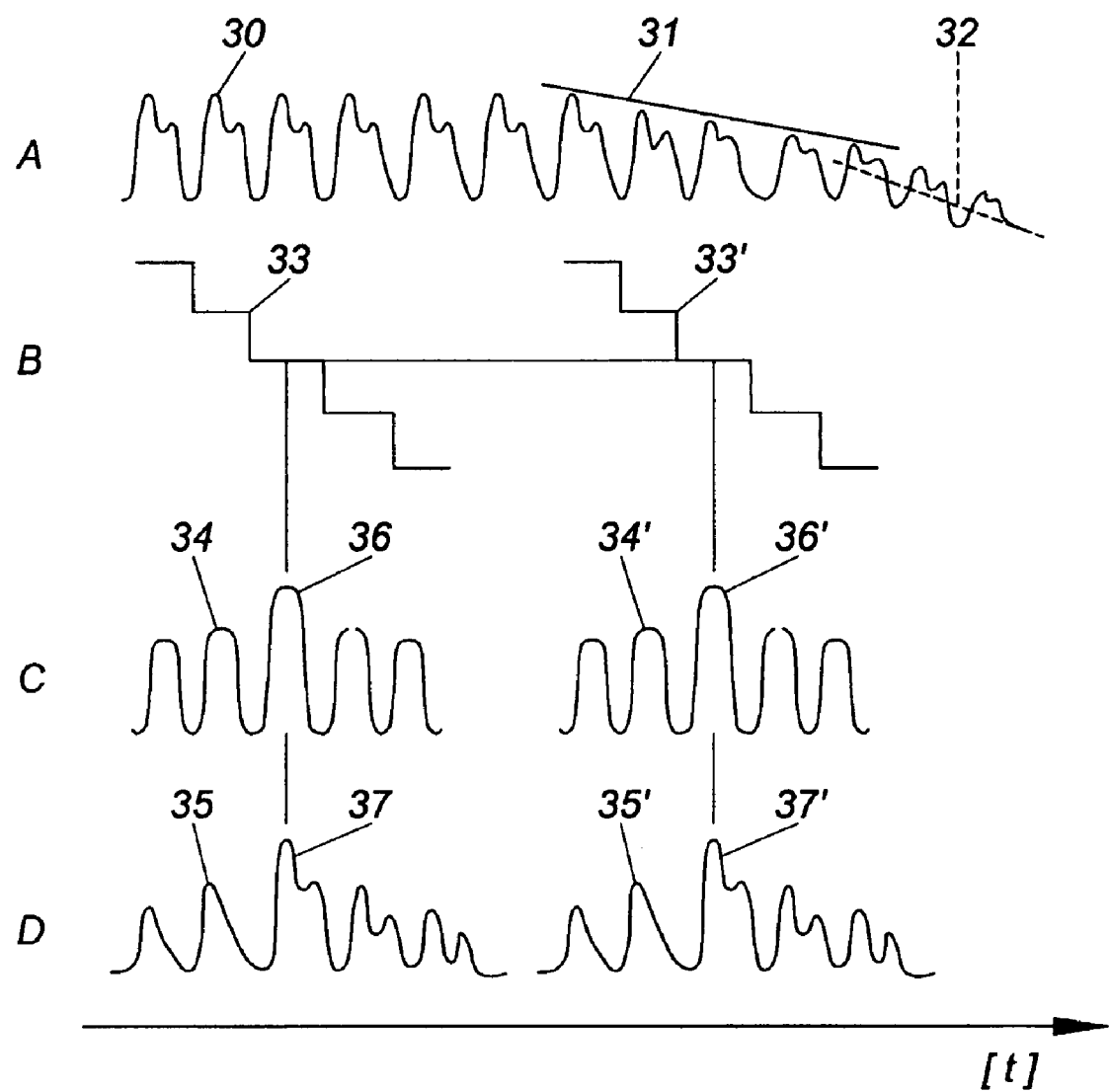
Figure 4:
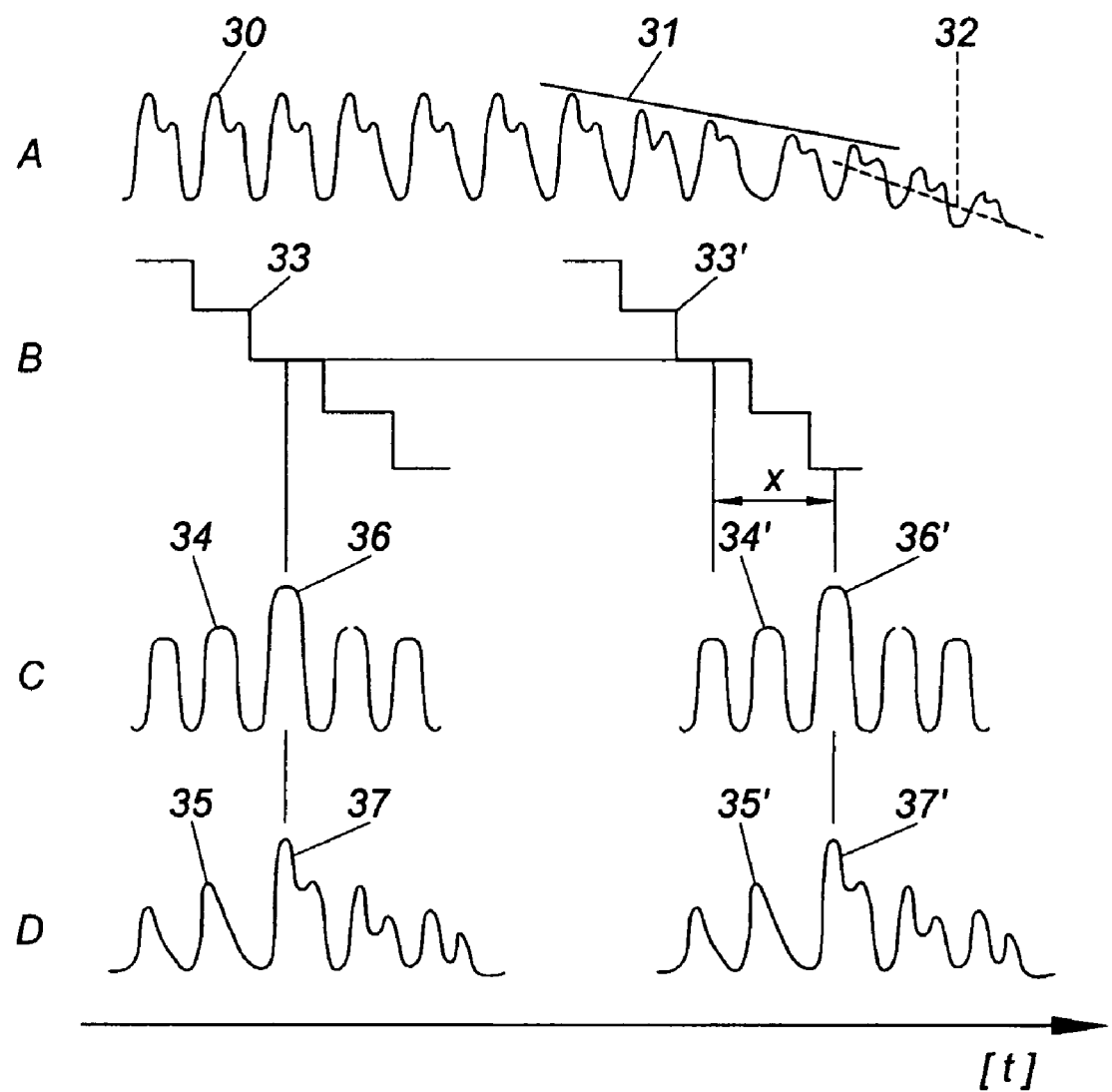

The diagrams A, B, C and D shown in FIGS. 3 and 4 have a common time axis t: on the ordinate of diagrams A, B and D pressure is plotted and on the ordinate of diagram C the intensity of the plethysmographic reference signal of the reference pressure chamber is plotted. If two pressure chambers are used, a pressure measuring chamber 4 and a reference pressure chamber 4', each in a pressure cuff, the diagrams C and D may be observed only alternatively, since the different functional states of the reference pressure chamber (watchdog pressure chamber), as described above, i.e. open-loop state (diagram C) and semi-closed-loop state (diagram D), can only be presented one after the other. If one pressure measuring chamber and two reference pressure chambers (three finger cuff) are used, both states and thus the diagrams C and D may be observed simultaneously. Any imprecision in the synchronicity of the curves in FIGS. 3 and 4 is only due to the drawing process. All curves in the drawings are corrected for base line drift.

Diagram A of FIG. 3 presents the typical pressure measuring signal 30 of the pressure measuring chamber in closed-loop operation showing a change in pressure amplitude 31 and in mean blood pressure 32 caused by drifting of the setpoint.

Diagram B shows an example of a preselectable pressure function 33, 33', e.g. the pressure steps of a consecutive staircase function, which is applied to the watchdog pressure chamber 4'. Diagram C shows the plethysmographic reference signal 34, 34' observed in the watchdog pressure chamber 4', of the plethysmographic sensor device 5', e.g. the signal of the light detector, and diagram D shows as an alternative the reference pressure signal 35, 35' in the watchdog pressure chamber 4', when the staircase function 33, 33' is applied, but now with simultaneously minimized amplitude of the reference signal 34, 34' (the so-called semi-closed-loop stair). While diagram C presents the volume amplitudes in the open-loop case, diagram D shows the pressure amplitudes in the semi-closed-loop case with minimized volume signal variation and additionally applied pressure steps of the staircase function. As can be seen from diagram C the amplitude variations of the reference signal 34 obtained from the watchdog pressure chamber show a localization in time: of the amplitudes and the amplitude maximum 36, 36' identical with that of identical applied pressures of the staircase function 33, 33'. The amplitude maximum 37, 37' in diagram D also exhibits identical localization at identical pressures of the consecutively applied staircase function 33, 33'.

The observed discrepancy, i.e. on the one hand a changing pressure amplitude 31 and changing mean pressure 32 in the closed-loop pressure chamber (diagram A), and on the other hand identical or closely similar localization of the amplitudes and amplitude maximum 36, 36' of the reference signal 34 (diagram C) at correspondingly equal pressure steps of the staircase function 33, 33' (diagram B) in the watchdog pressure chamber, respectively identical or similar localization of the pressure amplitudes 37, 37' of the reference pressure signal 35, 35' relative to pressure steps of the staircase function 33, 33' in the semi-closed-loop state, indicates a loss of setpoint and does not indicate a genuine drop of blood pressure. The watchdog pressure chamber 4' may be switched over automatically to act as closed-loop pressure measuring chamber 4 or vice versa, or the setpoint of the closed-loop pressure measuring chamber may be readjusted.

Switchover of watchdog pressure chamber to pressure measuring chamber, respectively readjustment of the setpoint in the pressure measuring chamber, should also occur, if the amplitude maximum 36, 36' in diagram C, or the maximum of the pressure amplitude 37, 37' in diagram D, exhibit a shift in a direction opposite to that of the pressure change measured in the closed-loop pressure measuring chamber (for instance a shift of the maximum amplitude 36, 36' of the reference signal 34 (open-loop) and the pressure amplitude 37, 37' (semi-closed-loop) in the watchdog pressure chamber towards higher pressures, while the mean pressure 32 or the blood pressure amplitude 31 in the pressure measuring signal 30 tend towards lower pressures).

FIG. 4 shows in diagram A the same change in pressure amplitude 31 and mean pressure 32 of the pressure measuring signal 30 as presented in FIG. 3, but in this instance caused by an actual pathological change in blood pressure. This can immediately be seen by the shift X of the maximum amplitude 36, 36' of the reference signal 34, 34' (diagram C, open-loop state), and alternatively from the maximum pressure amplitudes 37, 37' of the reference pressure signal 35, 35' (diagram D, semi-closed-loop state) measured in the watchdog pressure chamber, since the shift X of the position of the amplitude maxima in diagrams C and D occurs against the correspondingly equal pressure steps of the staircase function 33, 33' (diagram B). Diagram D shows—as in FIG. 3—the pressure amplitudes in the semi-closed-loop with minimized volume signal changes and additionally applied pressures of the staircase function. In the present case the maximum amplitude 36' of the reference signal 34' (diagram C, open-loop) and alternatively the maximum pressure amplitude 37' (diagram D, semi-closed-loop) is found at significantly lower blood pressure values. This unmistakably indicates a genuine drop in blood pressure and would immediately cause an optical and/or acoustical alarm to be raised by the alarm unit 18, if certain limit values were transgressed. Thus the present device is suitable for continuous blood pressure monitoring and will fulfil the strictest requirements.

Figure 5:
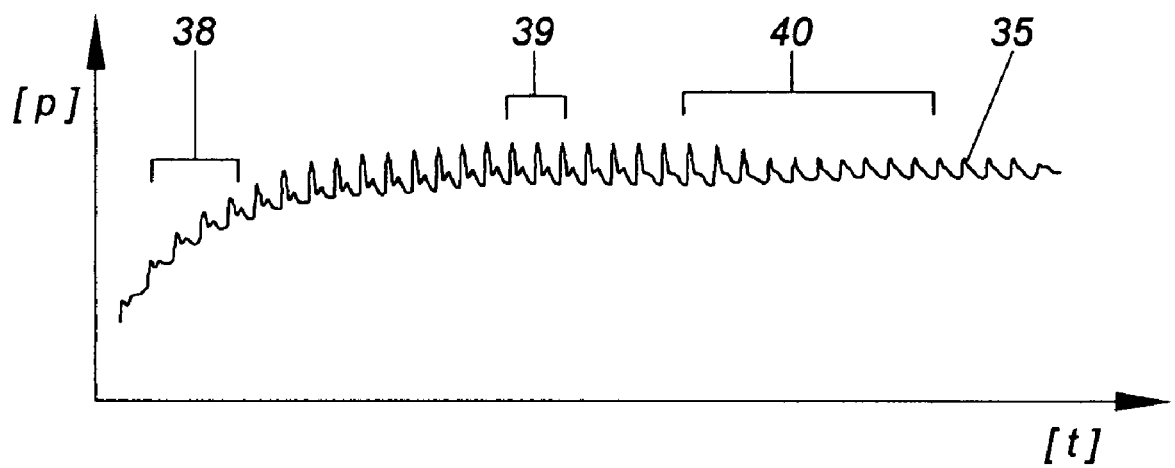
FIG. 3 to FIG. 5 are diagrams of measurement or pressure signals of the measuring device of the invention.

In FIG. 5 it is demonstrated that, besides the localization of the pressure amplitude, the shape of the curve in areas 38, 39, 40 of the reference pressure signal 35 of the semi-closed-loop measured in the reference pressure chamber, resp. the watchdog pressure chamber, with a pressure staircase function applied, also indicates whether a shift of the setpoint has occurred or not. As can be seen from FIG. 5, the shape of the pulse wave will change, depending on whether the pressure applied by the staircase function in the semi-closed-loop with minimization of the reference signal is too low 38, optimum 39 or too high 40. If the pressure in the watchdog pressure chamber is at its optimum the shape of the pressure curve corresponds closely to that of the physiological pressure curve known from invasive measurements, i.e. it has a steep ascending slope, a round peak, a dicrotic wave at a typical height of one half to two thirds of the pressure amplitude and an approximately exponential diastolic decay of the pulse curve, as shown at 39. If the pressure of the pressure staircase function is too low, however, the pulse curve in the semi-closed-loop will not only have smaller amplitude but will also lose its physiological shape, i.e. it will become flat and wide as shown at 38, and the dicrotic incision will shift in the direction of diastolic blood pressure. If the pressure of the pressure staircase function in the semi-closed loop is too high, area 40, the pulse curve has sharp peaks and the dicrotic wave no longer resembles the physiological pulse shape 39.

This means that besides the amplitude of the pressure wave also the shape of the pulse wave may be used to determine the optimum pressure value of the pressure staircase in the semi-closed-loop. For this purpose it will only be necessary to analyse the shape of the curve and to determine its deviation from a given ideal pulse curve. At that pressure of the pressure staircase in the semi-closed-loop at which the deviations of the measured pulse curve from an ideal pulse curve are minimal, the counter pressure equals the ideal counter pressure, with the transmural pressure $P_{Tm}$ approaching zero, and thus equals the setpoint value which must be set in the pressure measuring chamber. It is known that the physiological pulse shape changes with age or through the influence of atherosclerosis. In more rigid blood vessels the dicrotic wave is for instance shifted in the direction of the systolic peak and may even vanish completely in the peak. It may therefore be advantageous to store not only one but a plurality of physiological pressure curves in the microprocessor, with which the measured pulse curve in the semi-closed-loop is compared.

The pressure changes applied to the reference pressure chamber and the watchdog pressure chamber, respectively, are not restricted to the shape of a ramp or staircase; every other form of a given pressure function could be used under the method of the invention.

The variants described are to be taken as examples of the method and device according to the invention; a multitude of other embodiments can be imagined, such as for instance pressure cups instead of the pressure cuffs, which could be placed over the arteria radialis or the arteria temporalis. Dislocated pressure chambers placed on other body parts could also be considered, but would entail greater evaluation difficulties, since the pressure and flow situation of the blood is identical only in one and the same member and in similarly or identically dimensioned arteries. Besides the optical plethysmographic sensor device described, any other method of flow and volume measurement could be used.

It is further proposed that the pressure measurement in the small arteries, e.g. the finger arteries, is computationally adapted to the pressure in a large artery, which has been independently measured, since it is known that the pressure in small arteries is not necessarily equal to the pressure in large arteries. For this purpose the pressure in a large artery must be measured initially or intermittently by mean's of an independent device, and the continuous measurement of the blood pressure as described by the present invention must then be adapted in absolute value as regards systolic, as well as diastolic blood pressure to the pressure measured in the large artery.

If required, hydrostatic pressure between the pressure measurement chamber and/or reference pressure chamber (watchdog pressure chamber) on the one hand and the height of the heart on the other hand may be measured, e.g. with a fluid column, and the obtained pressure curve, as shown in diagram A of FIGS. 3 and 4, may be corrected for this hydrostatic pressure difference between pressure measuring chamber 4 and/or watchdog pressure chamber 4'. This will be of importance especially if the height relative to the heart of the body part to which the two pressure chambers 4, 4' or their pressure cuffs 1, 1' are attached, changes continuously.

Attention should also be paid to the fact that a body part, e.g. the finger 3, which is subjected to pressure, is in an uncontrollable way non-physiologically stressed by the continuously and rhythmically inflated pressure measuring chamber 4. Moreover, the setpoint of the pressure measuring chamber may be lost—despite the watchdog function of the reference pressure chamber—because partial occlusion by the pressure measuring chamber provokes physiological adaptations in the measured body part which differ from those in the body part subjected to the reference pressure chamber.

The resulting problems have a common cause, i.e., the blood flow in the measured body part, e.g. the finger, may on purely physiological grounds fluctuate by a factor 100. These large fluctuations of absolute blood flow will cause the blood pressure in small arteries to deviate from blood, pressure in large arteries. Low blood flow at the periphery of circulation, e.g. in the finger, is the consequence of a narrowing of the arterioles. This will cause strong reflection of the pulse wave at the narrows and thus a pressure increase in the smaller arteries compared to the pressure in the preceding larger artery. Vice versa open arterioles cause less reflection and will thus produce no or less pressure increase, possibly even a pressure decrease, compared to the preceding large arteries. If the change in volume or the absolute or relative blood flow at the periphery, e.g. in the finger, is known, the amount of reflection of the pressure wave in the arterioles following the pressure measuring chamber will also be known and the blood pressure value measured at the periphery may be corrected to obtain the absolute value in the large arteries.

Figure 6:
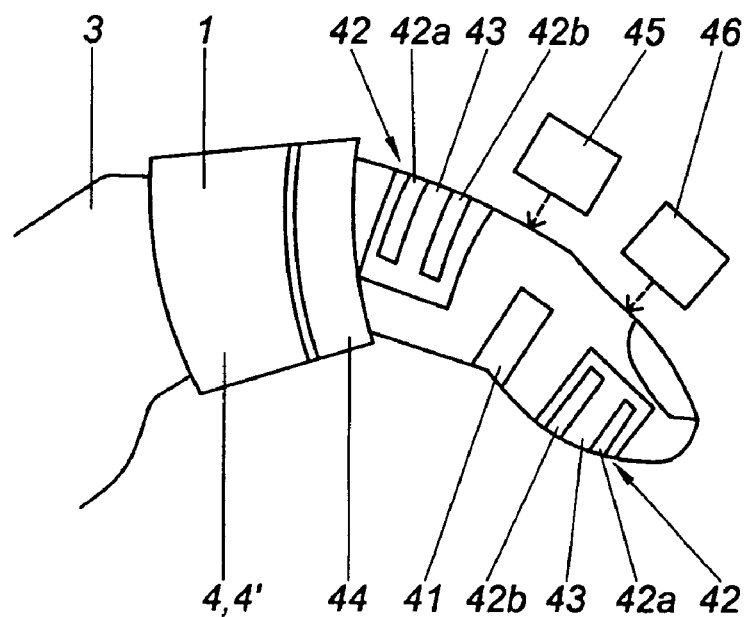
FIG. 6 is a schematic view with details of a further variant.

According to the invention at least one sensor 41, 42, 44—as shown in FIG. 6—may be provided in a position distal to the pressure measuring chamber 4 and/or the reference pressure chamber 4' to measure the volume change of the body part 3. The body part 3, preferably the distal end of the finger, may for instance be provided with an impedance sensor 42, a strain gauge 41 and/or an additional plethysmographic sensor 44. Preferably the volume change of the body part 3 is measured at a pressure of the pressure measuring chamber and/or the reference pressure chamber, which is less than arterial blood pressure, for instance 40 mm Hg. The change in volume of the body part distal to the pressure measuring chamber and/or the reference pressure chamber may then be used for the computational correction of the blood pressure that is continuously measured by the pressure measuring chamber.

The measurement accuracy of the method described may be further increased if distal to the pressure measuring chamber 4 and/or the reference pressure chamber 4' at least one sensor 45 for blood flow measurement is provided, for instance a venous occlusion plethysmograph or a Laser-Doppler-blood-flow measuring device.

Figure 7:
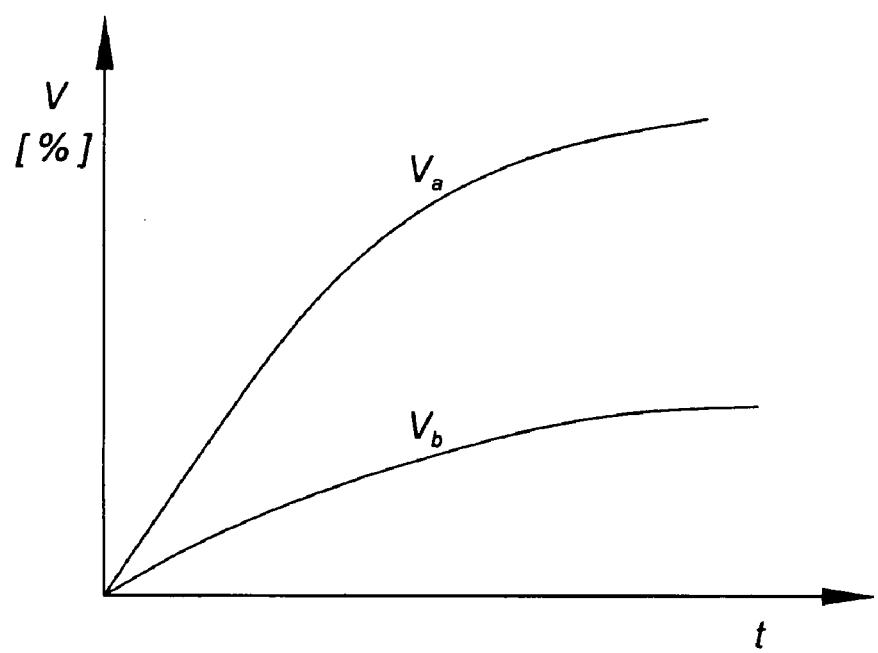
FIG. 7 is a diagram of the variant of FIG. 6.

As is schematically indicated in FIG. 6 at least one strain gauge 41—or a number of impedance electrodes 42—may be attached to the body part 3, e.g. the finger, which will continuously monitor the volume state of the relevant body part distal to the pressure cuff 1 and its measuring chamber 4. As regards the impedance electrodes it is to be noted that each of the outer electrodes 42a acts as current feed, while each inner electrode 42b serves for impedance measurement. A current and an impedance electrode could for instance be carried by a common supporting foil 43. When pressure is increased in the pressure measuring chamber 4 and/or in the reference pressure chamber 4', for instance to 40 mm Hg, blood will initially flow into the body part 3 only, but no longer back out of it: this causes a volume increase V of the body part over time t, as shown in the diagram of FIG. 7. A steep slope of the volume increase indicates high blood flow (volume curve $V_a$) and thus a correction of the blood pressure values different from that necessary at low blood flow (volume curve $V_b$). Low blood flow and slow volume increase result from contraction of the arterioles and indicate a stronger centrally directed reflection of the pulse wave and thus higher blood pressure values at the body part under investigation as compared to low flow and little volume increase of the body part. Correction of the blood pressure values in order to determine the blood pressure in the large arteries, which are of primary interest, is best performed on an empirical basis by determining the deviation of the blood pressure measured in the measuring chamber 4 from the blood pressure in a large artery which is simultaneously obtained by another conventional method, as a function of the percentage increase of volume of the body part distal to the pressure measuring chamber and/or the reference pressure chamber during the time the vein is closed.

It is of advantage to have information about the increase of volume and consequently about blood flow in the finger concerned, since—if the increase of volume is large—a quick exchange of pressure measuring chamber and reference pressure chamber may be effected, in order to avoid excessive filling and an edema in the body part concerned. If blood flow is low longer intervals between changes of pressure measuring chamber and reference measuring chamber will be possible.

Furthermore, a critical increase in the volume of the finger may also cause a loss of setpoint during blood pressure measurement in the pressure measuring chamber. This critical increase of volume may also be detected by measuring the finger volume, e.g. with a venous occlusion plethysmograph. Initially a rapid increase in volume is found, as long as the inflow of blood is not impeded; when the finger becomes congested the interior pressure of the tissue rises, which results in a slower increase in volume, but also in compression of the arteries and a decrease of the volume signal and thus loss of the setpoint of the pressure measuring chamber. This may be prevented by measuring the volume distally to the pressure measuring chamber and/or reference pressure chamber, and by changing the pressure measuring chamber 4 and/or reference pressure chamber 4', if critical changes in the filling curve of the measured body part are recognized.

According to a further development of the invention, there may be provided at a position distal to the pressure measuring chamber 4 and/or the reference pressure chamber 4' at least one sensor 46 for the measurement of blood gases, e.g. $CO_2$ or the partial pressure of $O_2$. The measurement of oxygen pressure or $CO_2$ concentration in the tissue may be used for controlling the pressure in the pressure measuring chamber 4 and/or the reference pressure chamber 4'.

Measuring the oxygen pressure or the carbon dioxide pressure distal to the pressure measuring chamber and/or the reference pressure chamber, for instance by means of known transcutaneous oxygen or carbon dioxide measuring devices, may be of advantage as a warning device indicating the necessity of changing or controlling the pressure measuring chamber and/or the reference pressure chamber, since a decrease of oxygen partial pressure and/or an increase of carbon dioxide pressure distal to the pressure measuring chamber and/or the reference pressure chamber, can signal swelling of the tissue and thus a threatening loss of setpoint.

Measuring the blood flow for instance in the finger has further advantages: a drop in blood pressure, for instance a life endangering state of shock, may on the one hand be caused by centralisation of circulation, e.g. due to loss of blood, with simultaneous reduction of blood flow in the periphery, i.e. in the finger. On the other hand shock may also occur due to excessive opening of the peripheral blood vessels, such that the filling volume of the circulation will no longer suffice to uphold blood pressure, as can for instance happen in septic shock. In this case blood flow in the periphery is high. The first form of shock needs therapy quite different, from that demanded by the second form. Thus the device of the invention may also be used for differential diagnosis of blood pressure drops and thus states of shock, which in turn will permit better therapy.

The invention claimed is:

1. A method for the continuous, non-invasive measurement of blood pressure based on the principle of the unloaded arterial wall, comprising positioning a first and a second pressure cuff of identical or comparable size with a first and a second inflatable pressure measuring chamber on at least one first and one second neighboring finger, each containing an artery of identical or comparable size, controlling pressure in the first pressure measuring chamber in dependence on a measurement signal of a plethysmographic sensor device in such a way that an amplitude of the plethysmographic measurement signal is minimized, obtaining a pressure measuring signal from the first pressure measurement chamber, operating the second pressure measuring chamber as a reference pressure chamber independently of the first pressure measuring chamber, controlling the pressure in the reference pressure chamber in dependence on a measurement signal of a second plethysmographic sensor device and in accordance with a preselectable pressure function, a reference signal being obtained simultaneously with the pressure measuring signal, and the reference signal used in the interpretation of the pressure measuring signal wherein an amplitude of said obtained reference signal is minimized while a reference pressure signal is measured, and analyzing the reference pressure signal, measured at various pre-selectable pressure values of the pressure function, compared to predetermined ideal pulse curves, and, when the deviation from a given pulse curve is at a minimum, determining the setpoint for the pressure measuring signal therefrom.

2. A method for the continuous, non-invasive measurement of blood pressure based on the principle of the unloaded arterial wall, comprising positioning a first and a second pressure cuff of identical or comparable size with a first and a second inflatable pressure measuring chamber on at least one first and one second neighboring finger, each containing an artery of identical or comparable size, controlling pressure in the first pressure measuring chamber in dependence on a measurement signal of a plethysmographic sensor device in such a way that an amplitude of the plethysmographic measurement signal is minimized, obtaining a pressure measuring signal from the first pressure measurement chamber, operating the second pressure measuring chamber as a reference pressure chamber independently of the first pressure measuring chamber, controlling the pressure in the reference pressure chamber in dependence on a measurement signal of a second plethysmographic sensor device and in accordance with a preselectable pressure function, a reference signal being obtained simultaneously with the pressure measuring signal, and the reference signal used in the interpretation of the pressure measuring signal, and inferring a physiological or pathological change of the pressure measuring signal from a change of a mean pressure and/or amplitude of the pressure measuring signal and a shift of amplitude maximum of the reference signal or the reference pressure signal in the same direction.

3. A method for the continuous, non-invasive measurement of blood pressure based on the principle of the unloaded arterial wall, comprising positioning a first and a second pressure cuff of identical or comparable size with a first and a second inflatable pressure measuring chamber on at least one first and one second neighboring finger, each containing an artery of identical or comparable size, controlling pressure in the first pressure measuring chamber in dependence on a measurement signal of a plethysmographic sensor device in such a way that an amplitude of the plethysmographic measurement signal is minimized, obtaining a pressure measuring signal from the first pressure measurement chamber, operating the second pressure measuring chamber as a reference pressure chamber independently of the first pressure measuring chamber, controlling the pressure in the reference pressure chamber in dependence on a measurement signal of a second plethysmographic sensor device and in accordance with a preselectable pressure function, a reference signal being obtained simultaneously with the pressure measuring signal, and the reference signal used in the interpretation of the pressure measuring signal, and inferring a loss of setpoint of the pressure signal from a change of the mean pressure and/or the amplitude of the pressure measuring signal and an absent or oppositely directed shift of the amplitude maximum of the reference signal or the reference pressure signal.

4. A method for the continuous, non-invasive measurement of blood pressure based on the principle of the unloaded arterial wall, comprising positioning a first and a second pressure cuff of identical or comparable size with a first and a second inflatable pressure measuring chamber on at least one first and one second neighboring finger, each containing an artery of identical or comparable size, controlling pressure in the first pressure measuring chamber in dependence on a measurement signal of a plethysmographic sensor device in such a way that an amplitude of the plethysmographic measurement signal is minimized, obtaining a pressure measuring signal from the first pressure measurement chamber, operating the second pressure measuring chamber as a reference pressure chamber independently of the first pressure measuring chamber, controlling the pressure in the reference pressure chamber in dependence on a measurement signal of a second plethysmographic sensor device and in accordance with a preselectable pressure function, a reference signal being obtained simultaneously with the pressure measuring signal, and the reference signal used in the interpretation of the pressure measuring signal, and wherein at preselectable time intervals or triggered by loss of setpoint the reference pressure chamber is operated as pressure measuring chamber and the pressure measuring chamber as reference pressure chamber.

5. Method according to claims 1, 2, 3 or 4 comprising continuously monitoring and/or adjusting a setpoint of the pressure measuring signal by means of the reference signal.

* * * * *